United States Patent [19]

Mrozik

[11] Patent Number: 4,457,920
[45] Date of Patent: Jul. 3, 1984

[54] 4A-SUBSTITUTED AVERMECTIN COMPOUNDS

[75] Inventor: Helmut H. Mrozik, Matawan, N.J.

[73] Assignee: Merck & Co., Inc., Rahway, N.J.

[21] Appl. No.: 404,960

[22] Filed: Aug. 4, 1982

Related U.S. Application Data

[63] Continuation-in-part of Ser. No. 298,861, Sep. 3, 1981, abandoned.

[51] Int. Cl.³ .................. A61K 31/365; C07D 493/22
[52] U.S. Cl. .................................... 424/180; 424/263; 424/274; 424/279; 549/264; 548/407; 546/15; 536/7.1
[58] Field of Search ............... 424/180, 263, 274, 279; 549/264; 536/7.1; 546/15; 548/407

[56]  References Cited

U.S. PATENT DOCUMENTS

| 3,950,360 | 4/1976  | Aoki et al.     | 424/279 |
| 4,156,720 | 5/1979  | Fisher et al.   | 424/180 |
| 4,173,571 | 11/1979 | Chabala et al.  | 549/264 |
| 4,199,569 | 4/1980  | Chabala et al.  | 424/180 |
| 4,201,861 | 5/1980  | Mrozik et al.   | 424/180 |
| 4,206,205 | 6/1980  | Mrozik et al.   | 424/181 |

FOREIGN PATENT DOCUMENTS 1573955  8/1980  United Kingdom ............... 424/180

Primary Examiner—Jane T. Fan
Attorney, Agent, or Firm—David L. Rose; Mario A. Monaco; Michael C. Sudol, Jr.

[57] ABSTRACT

There are disclosed novel avermectin compounds wherein the 4-methyl group is substituted with hydroxy or various groups connected through the hydroxy oxygen atom. The hydroxy compounds are prepared by oxidation of the 4-methyl group and the hydroxy substituents prepared by a substitution process selective for primary alcohols. The compounds have utility as antiparasitic agents and compositions for that use are also disclosed.

11 Claims, No Drawings

4A-SUBSTITUTED AVERMECTIN COMPOUNDS

CROSS REFERENCE TO RELATED APPLICATIONS

This application is a continuation-in-part of my co-pending application Ser. No. 298,861 filed Sept. 3, 1981 now abandoned.

BACKGROUND OF THE INVENTION

The term avermectin (previously referred to as C-076) is used to describe a series of compounds isolated from the fermentation broth of a avermectin producing strain of *Streotomyces avermitilis*. The morphological characteristics of the culture are completely described in Great Britain Pat. No. 1,573,955. The avermectin compounds are a series of macrolides, each of which is substituted thereon at the 13-position with a 4-(α-L-oleandrosyl)-α-L-oleandrose group. The avermectin compounds and the instant derivatives thereof have a very high degree of anthelmintic and antiparasitic activity.

The avermectin series of compounds have the following structure:

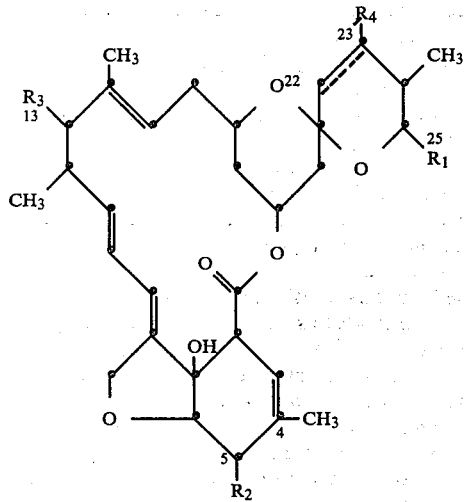

wherein
$R_1$ is iso-propyl or sec-butyl; and
$R_2$ is methoxy or hydroxy;
$R_3$ is the 4'-(α-L-oleandrosyl)-α-L-oleandrosyloxy group of the structure:

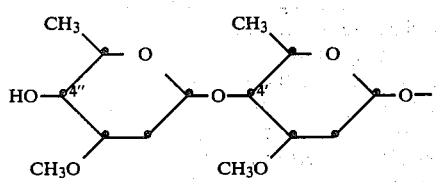

and wherein the broken line indicates a single or a double bond;
$R_4$ is hydroxy and is present only when said broken line indicates a single bond.

There are eight different avermectin compounds and they are given the designations A1a, A1b, A2a, A2b, B1a, B1b, B2a, B2b based upon the structure of the individual compounds.

In the foregoing structural formula, the individual avermectin compounds are as set forth below.

|     | $R_4$       | $R_1$     | $R_2$   |
|-----|-------------|-----------|---------|
| A1a | Double bond | sec-butyl | —OCH$_3$ |
| A1b | Double bond | iso-propyl| —OCH$_3$ |
| A2a | —OH         | sec-butyl | —OCH$_3$ |
| A2b | —OH         | iso-propyl| —OCH$_3$ |
| B1a | Double bond | sec-butyl | —OH     |
| B1b | Double bond | iso-propyl| —OH     |
| B2a | —OH         | sec-butyl | —OH     |
| B2b | —OH         | iso-propyl| —OH     |

The methyl group at the 4-postion of the avermectin macrolide ring is referred to as the 4a carbon atom. The substitution at the 4a position is the subject matter of this invention.

Avermectin compounds, with a hydrogen at the 13-position rather than the oxygen atom which is bonded to the disaccharide moiety, as disclosed in U.S. Pat. Nos. 4,171,134 and 4,173,571 by Chabala et al., are closely related to the milbemycin compounds disclosed in U.S. Pat. No. 3,950,360 to Aoki et al. Such compounds have a methyl or ethyl group at the 25-position rather than the instant isopropyl or sec-butyl group. The compounds, as described in the Aoki et al., patent, are produced by an organism of the genus Streptomyces, strain B-41-146. Certain of the milbemycin compounds are subject to the modifications at the 4a-position of this invention and the structures of such compounds are set forth below. The $R_1$, $R_2$ and $R_3$ designations refer to the above formula.

| Milbemycin | $R_3$ 13-position | $R_4$ | $R_1$  | $R_2$   |
|------------|-------------------|-------|--------|---------|
| α1         | —H                | —H    | methyl | —OH     |
| α2         | —H                | —H    | methyl | —OCH$_3$ |
| α3         | —H                | —H    | ethyl  | —OH     |
| α4         | —H                | —H    | ethyl  | —OCH$_3$ |

SUMMARY OF THE INVENTION

The instant invention is concerned with certain derivatives of avermectin compounds wherein the 4-methyl group is substituted with hydroxy and said 4a-hydroxy group is variously substituted. Thus, it is an object of the instant invention to describe such 4a-hydroxy compounds and derivatives thereof. A further object is to describe processes for the preparation of such compounds. A still further object is to describe the uses of such compounds as antiparasitic agents. Still further objects will become apparent from a reading of the following description.

DESCRIPTION OF THE INVENTION

The compounds of the instant invention have the following structural formula:

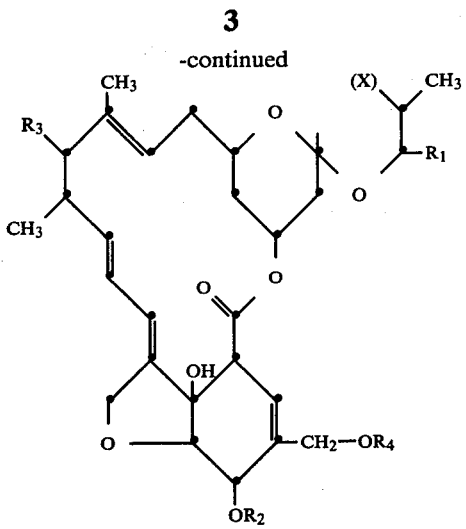

wherein
X is

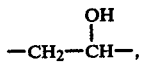

—CH₂—CH₂—, —CH=CH—, or

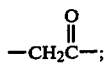

$R_1$ is methyl, ethyl, isopropyl or sec-butyl
$R_2$ is hydrogen, methyl, acetyl, phenoxyacetyl or t-butyl dimethylsilyl;
$R_3$ is hydrogen, hydroxy, acetoxy, α-L-oleandrosyloxy, 4'-acetyl-α-L-oleandrosyloxy, 4'-(α-L-oleandrosyl)-α-L-oleandrosyloxy, 4''-acetyl-4'-(α-L-oleandrosyl)-α-L-oleandrosyloxy, or 4''-(phenoxyacetyl)-4'-(α-L-oleandrosyl)-α-L-oleandrosyloxy; and $R_4$ is hydrogen, acetyl, benzoyl, pyridinylcarbonyl, pyrrollylcarbonyl, —CO(CH₂)ₙCOOH or —CO(CH₂)ₙCOOM wherein n is 2, 3 or 4 and M is an alkali metal or an ammonium or diloweralkyl ammonium cation; provided that $R_4$ is pyrrollylcarbonyl only when $R_1$ is isopropyl or sec-butyl.

Examples of preferred compounds of the instant invention are:
4a-hydroxy avermectin A2a/A2b
4a-[(3-pyridinylcarbonyl)oxy]-22,23-dihydro avermectin B1a/B1b
4a-[(2-prrolylcarbonyl)oxy]-22,23-dihydro avermectin B1a/B1b
4a-hydroxy-22,23-dihydro avermectin B1a/B1b
4a-benzoyloxy-22,23-dihydro avermectin B1a/B1b
4'',5-di(phenoxyacetyl)-4a-hydroxy avermectin B1a/B1b
4'',5-di(phenoxyacetyl)-4a-acetoxy avermectin B1a/B1b
5,13-diacetyl-4a-hydroxy-22,23-dihydro avermectin B1a/B1b aglycone
5,13-diacetyl-4a-acetoxy-22,23-dihydro-avermectin B1a/B1b aglycone
13-acetyl-4a-acetoxy-22,23-dihydro-avermectin B1a/B1b aglycone
4'',5-di(phenoxyacetyl)-4a-hydroxy-22,23-dihydro avermectin B1a/B1b
4a-hydroxy-13-deoxy-22,23-dihydro-avermectin B1a/B1b aglycone
4a-hydroxy milbemycin α₁
4a-hydroxy milbemycin α₃
4a-hydroxy-4a-[3-[(2,2,2-trichloroethoxy)carbonyl]-propanoyl]milbemycin α₁
4a-hydroxy-4a-succinoyl milbemycin α₁

The "b compounds", those with a 25-isopropyl group are very difficult to separate from the corresponding "a compound", with a 25-sec-butyl group and as such the compounds are isolated as mixtures of the two compounds. Thus, references in the instant application to "a compounds" such as B1a, A1a, and the like, are construed to actually contain a certain proportion of the corresponding "b compound" such as B1b, A1b, and the like. In practice, this proportion has been seen to be up to 20% of the "b" isomer. The nomenclature of this application generally is to use a slash (/) to designate that either compound alone or a mixture thereof is intended.

The 4a-hydroxy compounds are prepared by oxidizing the 4a-unsubstituted compounds. The acyl substituents on the 4a-oxygen are prepared by reacting the appropriate acyl containing compound with said 4a-hydroxy compound.

The oxidation of the 4-methyl group must be carried out selectively. Although the 4-methyl is an allylic methyl group and thus susceptible to oxidation, there is another allylic methyl group present on the molecule, such as that at the 14 position. In addition, there are numerous allylic methine protons, such as those at the 2, 6, 8a, 12, 13, 16 and 24, positions which are capable of being oxidized by mild oxidation agents. Thus, it was surprising that a process could be developed that was selective for the desired oxidation product.

The preferred process involves treating the 4-methyl compound with t-butyl hydroperoxide in the presence of a catalytic amount of selenium dioxide. Under these conditions the selenium dioxide actually oxidizes the 4-methyl to a 4a-hydroxy methyl and is itself oxidized in the process. The t-butyl hydroperoxide oxidizes the reduced selenium compounds back to selenium dioxide for further oxidation of the molecule. In this way only a small, catalytic amount of the selenium dioxide is required.

The reaction is carried out in an inert solvent; one not susceptible to oxidation. Methylene chloride is preferred, however, ethyl acetate, tetrahydrofuran and the like may also be employed. The reaction temperature may be from 0° to 50° C., however, reaction at room temperature is preferred. Under these conditions the reaction is generally complete in from 1–48 hours, however, under the preferred condition the reaction is generally complete in about 24 hours.

Where the starting material contains a 5-hydroxy group, such group may be advantageously protected to avoid reduced yields due to the oxidation thereof to a keto group.

The preparation of the 4a-hydroxy derivatives and the subsequent substitution thereof by $R_4$ are outlined in the following reaction scheme:

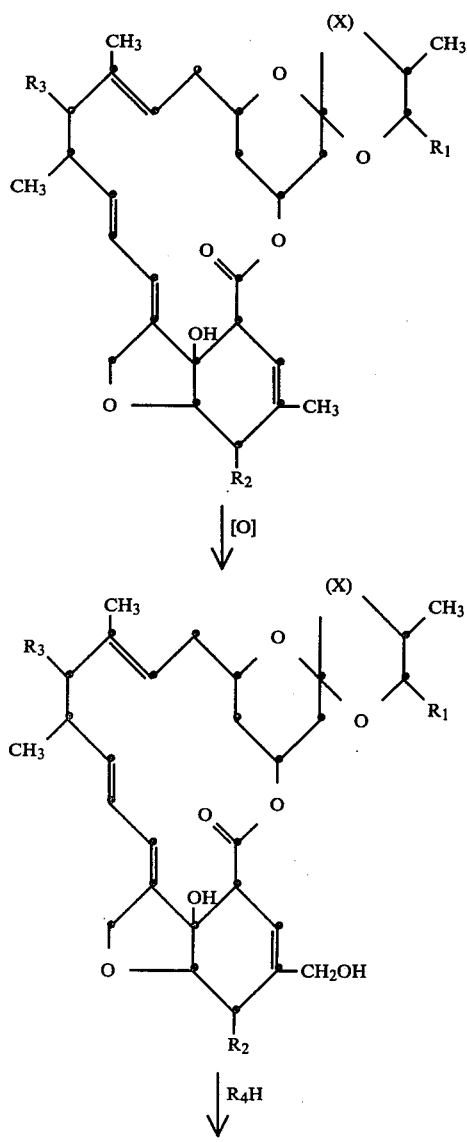

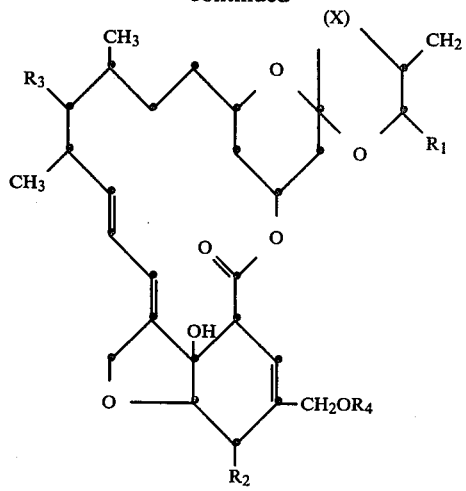

wherein $R_1$, $R_2$, $R_3$, $R_4$ and X are as defined above.

The substitution at the 4a-hydroxy to prepare the 4a-OR$_4$ substituted compounds is carried out using a process which is selective for primary alcohols. Thus, the remaining hydroxy groups, which are either secondary or tertiary are not affected and need not be protected. The reaction is carried out preferably using the $R_4$-H compound and the reagents triphenylphosphine and a diloweralkyl diazodicarboxylate. The methyl and ethyl esters of the reagent are generally preferred. The starting 4a-hydroxy compound, the $R_4$-H compound and the reagents are combined in an inert solvent such as benzene, toluene, tetrahydrofuran, ethylacetate and the like at from −15° to 80° C. for from 5 minutes to 5 hours. It is preferred to carry out the reaction in toluene at about room temperature whereupon the reaction is generally complete in about 20 minutes.

PREPARATION OF STARTING MATERIALS

The ultimate starting materials for the compounds of this invention are the avermectin fermentation products defined above. Thus it is apparent that additional reactions are required to prepare the instant compounds. Specifically, substituent groups are prepared at the 4″, 4′, 5, 13, 22 and 23 positions. It is generally preferred to prepare whatever substituents are required at these positions before the oxidation at the 4-methyl and subsequent substitution at the 4a-hydroxy are carried out. Such a procedure generally avoids undesirable side-reactions. This technique is not required however, and, if desired, other sequences may be used.

In addition, during certain reactions it may be necessary to protect certain functions, such as hydroxy groups, to avoid other undesired side reactions. Such protecting groups may then be removed although certain protected positions, such as acyl substitutions at the 5, 4″, 4′, and 23 positions are included within the ambient of this invention. A discussion of the various procedures used to prepare the substituents of the instant compounds at positions other than the 4a position, and the procedures used to protect susceptible functionalities follows:

As is readily apparent from an analysis of the structure of the avermectin starting materials, there are five unsaturations in the 1-series of compounds. Thus, in the 1-series of compounds, it is necessary to reduce the 22,23-double bond while not affecting the remaining four unsaturations or any other functional group present on the molecule in order to prepare 22, 23-dihydro avermectins used as starting materials for this invention. It is necessary to select a specific catalyst for the hydrogenation, one that will selectively hydrogenate the least hindered from among a series of unsaturations. The preferred catalyst for such a selective hydrogenation procedure is one having the formula:

$$[(R_5)_3P]_3RhY$$

wherein $R_5$ is loweralkyl, phenyl, or loweralkyl substituted phenyl and Y is a halogen. The reduction procedure is completely described in U.S. Pat. No. 4,199,569 to Chabala et al.

In the preferred catalyst $R_5$ is phenyl and Y is chlorine, that is the compound tris(triphenylphosphine)-rhodium (I) chloride, which is also known as Wilkinson's homogeneous catalyst.

The reaction is carried out using a small amount of the catalyst. The amount of catalyst is not critical and from 0.05 to 0.5 moles of the catalyst for each mole of starting material have been successfully employed. Molar ratios in the range of 0.25 to 0.40 are preferred.

The hydrogenation is carried out in a hydrogen atmosphere which may be either at atmospheric pressure or up to about 4 atmospheres pressure in a standard laboratory hydrogenation apparatus. A solvent is normally employed to dissolve both the starting materials and the catalyst. Preferred solvents are hydrocarbon solvents such as benzene, toluene, petroleum ether and other alkane hydrocarbons. The reaction is complete when the calculated amount of hydrogen has been taken up by the reaction. This will generally require from about 1 to 48 hours. The reaction may be carried out at from room temperature to about 75° C., however, room temperature is preferred. The hydrogenation products are isolated and purified by techniques known to those skilled in the art.

Other reactions may be carried out on the avermectin starting materials or on the hydrogenated products to prepare the compounds of this invention. While it is possible to complete all of the other reactions on the avermectin starting material and have the hydrogenation step as the final reaction, it is preferred to carry out the hydrogenation step first. Because the 22,23-double bond is somewhat susceptible to nucleophilic addition, reaction conditions for removing the sugar groups or acylating the hydroxy groups must be carefully controlled if the 22,23-double bond is present. If the 22,23-double bond is hydrogenated first, the subsequent sugar removal and acylation is rendered more facile.

Thus, the additional reactions which may be carried out to prepare the compounds of this invention are the selective removal of one or both of the α-L-oleandrosyl moieties (described in U.S. Pat. No. 4,206,205 to Mrozik et al.) or the selective acylation of the susceptible hydroxy groups (described in U.S. Pat. No. 4,201,861 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

When this procedure is employed on the starting material (the compounds with the 22,23-double bond) there is a possibility of nucleophilic addition to the double bond. If such occurs, chromatographic purification will remove the by-product in order to allow for further reactions.

The acids listed above are appropriate for this process, and again sulfuric acid is the preferred acid.

The above described compounds are isolated from the reaction mixture and mixtures of compounds are separated using techniques known to those skilled in this art, and in particular the chromatographic techniques described above.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures.

The acylation reagents employed are generally the halide, preferably the chloride, of the above loweralkanoyl groups. That is the loweralkanoyl halide reagent is generally employed.

In addition, the acylation reagent could be in the form of the anhydride or of the halo formate. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethylamine and the like. The basic compound is required in equimolar amounts relative to the numbered moles of hydrogen halide being liberated, however excess amounts, even using the basic compound as a solvent, are not detrimental.

In the case of the A1 compounds of avermectin, or of the hydrogenated avermectin A1 compounds there is only a single hydroxy group, 4" hydroxy, which may be acylated. The formation of the monosaccharide or the aglycone still leaves only a single hydroxy group which may be acylated, that is the 4' or 13 hydroxy group.

In the case of the 4", 4' and 13 hydroxy groups of avermectin A1 compounds, the acylating reagent is dissolved in a suitable solvent, pyridine is preferred, and the acylating reagent added. The reaction is maintained at from 0° C. to room temperature for from 4 to 24 hours. The product is isolated using known techniques.

The A2 compounds have two available hydroxy groups, the 4"(4' or 13) or the 23 positions. The different hydroxy groups may be selectively acylated by controlling the reaction conditions.

The 4"(4' or 13) monoacyl compound may be prepared by using the reaction conditions described above for the A1 compound. Since the 23 hydroxy is less reactive than the 4"(4' or 13) position, mild reaction conditions (0° C.) will afford predominantly the monoacyl compound. Heating the reaction mixture at from room temperature to 100° C. for from 1 to 24 hours will produce the 4"(4' or 13), 23-diacyl compound. If the 23 monoacyl compound is desired, the diacyl compound is treated with aqueous base, such as sodium hydroxide, at room temperature for from 1 to 24 hours. The 4"(4' or 13) acyl group will be hydrolyzed leaving the 23 monoacyl compound.

The B1 compounds have 2 available hydroxy groups: at the 4"(4' or 13) and the 5-positions. However, the two hydroxy groups have similar reactivities. When the reaction of the acylating agent in pyridine is carried out at about room temperature for from 4 to 24 hours, the diacyl compound is recovered. When the reaction is carried out at 0° C. a mixture of the 4"(4' or 13) and 5 monoacyl compounds are recovered. To recover individual compounds, the mixture is placed on a chromatographic column or a preparative layer chromatographic plate of alumina or silica gel and the individual compounds are readily isolated. In addition, techniques such as high pressure liquid chromatography may be employed to separate mixtures of acylated compounds.

The B2 compounds have three hydroxy groups available for substitution: the 4"(4' or 13), 5 and 23 positions. The relative reactivity of the various hydroxy groups is the same as in the other series of compounds. Thus, the triacyl compound may be prepared by carrying out the reaction at from room temperature to 100° C. The 4"(4' or 13), 5 diacyl compound may be prepared by carrying out the reaction at no more than room temperature. At 0° C. a mixture of 4"(4' or 13), and 5 monoacyl compounds is recovered which is separable as described above. By varying the reaction conditions and sequence, and by hydrolyzing the undesired acyl groups, all combinations of mono and diacyl compound may be recovered. For example, to prepare the 23-acyl compound, the triacyl compound is hydrolyzed with aqueous base as described above to remove the 4"(4' or 13) and 5 acyl groups. Acylation of the 23 monoacyl compound at 0° C. will result in a mixture of the diacyl compounds which is readily separable.

The 13-position substituents (R$_3$=halogen, hydrogen) are prepared from the avermectin starting materials as described hereinbelow. The reaction at the 13-position can generally be carried either before or after the other above described reactions.

The series of reactions at the 13-position commences with the removal of the α-L-oleandrosyl-α-L-oleandrose side chain which is found in the avermectin starting materials. This reaction produces what is identified as the "avermectin aglycone" compounds characterized by having a hydroxy group at the 13-position. The avermectin aglycone compounds are then halogenated with a suitably reactive benzenesulfonyl chloride or bromide in the presence of a base to produce the "13-deoxy-13-halo-avermectinaglycone" compounds. The halogen is then removed in a reaction with a trialkyltinhydride to produce the "13-deoxy-avermectin aglycone compounds." The aglycone compounds are prepared using procedures described above.

The procedures for the preparation of the 13-deoxy compounds are described in detail in U.S. Pat. Nos. 4,171,134 and 4,173,571 to Chabala et al.

The 23-hydroxy group is oxidized to the 23-keto group to form the compounds wherein X is

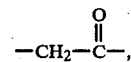

using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydride-dimethylsulfoxide; chromic acid-acetic acid; and the like. Oxalylchloride-dimethylsulfoxide is the preferred oxidizing agent. Suitably protected compounds, as described below, are employed. The reaction is carried out at from dry-ice bath temperatures to room temperature, preferably from dry-ice bath temperatures to 0° C. and is complete in from 1-24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

In the following description of the preparation of the protected compounds, it is noted that such protected compounds are novel and have considerable antiparasitic activity. These protected derivatives are included within the ambit of the instant invention.

In order to avoid unwanted side-reactions, it is important that, in those avermectin compounds with a hydroxy group at the 5-position (the B-series of compounds), and to a lesser extent, the 23-hydroxy group of the 2-series of compounds, said hydroxy groups be protected. The protecting group is ideally one which may be readily synthesized, will not be affected by the reactions to alter the substituents, at other positions and may be readily removed without affecting any other function of the molecule. One preferred type of protecting group for the avermectin type of molecule is the trisubstituted silyl group, preferably a trialkylsilyl group. One preferred example is the tert-butyldimethylsilyl group. The reaction is carried out by reacting the hydroxy compound with the appropriately substituted silyl halide, preferably the silyl chloride, in an aprotic polar solvent such as dimethylformamide. Imidazole is added as a catalyst. The reaction is complete in from ½ to 24 hours at from 0°–25° C. For the 5-position hydroxy group of the reaction is complete in about ½ to 3 hours at from 0° C. to room temperature. The silylation reaction is much slower at the 23-position hydroxy group (the 2-series of compounds), then at the 5-position hydroxy group, and protection is generally not necessary. However, if it is desired to protect the 23-hydroxy group, the reaction will be complete in about 5 to 24 hours at from about room temperature to 75° C. This reaction is selective to the 5- and 23-positions under the conditions above described, and very little, if any, silylation is observed at other hydroxy substituted positions.

The silyl group may be removed after the other contemplated reactions have been carried out. The silyl group or groups are removed by stirring the silyl compound in methanol catalyzed by a catalytic amount of an acid, preferably a sulfonic acid such as p-toluenesulfonic acid. The reaction is complete in about 1 to 12 hours at from 0° to 50° C.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active monosaccharide or aglycone avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasties is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitc diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual hydrogenated avermectin components may be used, as well as mixtures of the parent avermectin compounds other avermectin compound or other active compounds not related to avermectin and the compounds of this invention.

In the isolation of the avermectin compounds, which serve as starting materials for the instant proceses, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin Bla or Ala and 20% avermectin Blb or Alb. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in Great Britain Pat. No. 1,573,955. The preparation of the acylated avermectin compounds is described in U.S. Pat. No. 4,201,861 issued May 6, 1980. The selective 22,23-dihydro derivatives of avermectin compounds are described in U.S. Pat. No. 4,199,569 issued Apr. 22, 1980. The monosaccharide and aglycone derivatives of avermectin compounds are described in U.S. Pat. No. 4,206,205 issued Jan. 3, 1980. The 13-deoxy avermectin compounds and the 13-halo precursors therefor are described in U.S. Pat. No. 4,173,571 issued Nov. 6, 1979, and in U.S. Pat. No. 4,171,314 issued Oct. 16, 1979.

EXAMPLE 1

4a-Hydroxy Avermectin A2a/A2b 5.5 Mg of selenium dioxide are suspended in 0.3 ml of methylene chloride and combined with 22 μl of 90% t-butyl hydroperoxide and stirred at room temperature for 30 minutes. 90 Mg of avermectin A2a/A2b dissolved in 0.2 ml of methylene chloride is added and the reaction mixture is stirred at room temperature for 24 hours. The reaction mixture is combined with 4 ml of water and 3 ml of ether, shaken and the layers separated. The aqueous layer is extracted twice more with 2 ml portions of ether and the combined extracts are washed 3 times with 1 ml portions of water, dried over magnesium sulfate and evaporated to dryness under a stream of nitrogen affording 89 mg of a pale yellow foam. The yellow foam is dissolved in a minimum amount of methylene chloride and placed equally on 3 silica gel preparative layer chromatography plates coated with 0.5 mm of silica gel. The plates are eluted with a 2:1 mixture of ethyl acetate and methylene chloride twice and the bands separated. The product is extracted from the silica gel with ethyl acetate affording 28.8 mg of a pale yellow solid which is identified by nuclear magnetic resonance, mass spectrometry and ultraviolet spectroscopy as 4a-hydroxy avermectin A2a/A2b.

EXAMPLE 2

4a-Hydroxy Avermectin B1a/B1b 55 mg of selenium dioxide is combined with 5 ml of methylene chloride and 0.225 ml of 90% t-butyl hydroperoxide stoppered and stirred at room temperature for 30 minutes. 870 mg of avermectin B1a/B1b is added and the reaction mixture is stoppered and stirred at room temperature for 24 hours. 35 ml of water and 30 ml of ether is added and the reaction mixture is shaken and the layers separated. The aqueous layer is extracted twice more with 15 ml portions of ether and the ether layers are combined and washed with four 10 ml portions of water. The ether layer is dried over magnesium sulfate and concentrated to dryness in vacuo affording 990 mg of a light yellow foam. The foam is dissolved in methylene chloride and placed equally on 5 preparative layer chromatography plates coated with 2 mm of silica gel and eluted with 7% methanol in methylene chloride twice. The bands containing the product are separated and extracted with ethyl acetate and evaporated to dryness in vacuo. The major band closest to the origin afforded 320 mg of an off-white yellow foam which is identified by nuclear magnetic resonance, mass spectrometry and ultraviolet spectroscopy as 4a-hydroxy avermectin B1a/B1b.

EXAMPLE 3

22,23-Dihydro-4a-hydroxy Avermectin B1a/B1b

Following the procedure of Example 1 using 190 mg of selenium dioxide, 0.76 ml of 90% t-butyl hydroperoxide and 3 gms of 22,23-dihydro avermectin B1a/B1b, there is obtained 3.2 gms of 22,23-dihydro-4a-hydroxy avermectin B1a/B1b as crude material which is purified on a column of 105 gms of silica gel and eluted with 4% methanol in methylene chloride affording 1.27 gms. of product which is identified using nuclear magnetic resonance and mass spectroscopy.

EXAMPLE 4

22,23-Dihydro-4a-(2-pyrrolecarbonyloxy) Avermectin B1a/B1b 50 mg of 22,23-dihydro-4a-hydroxy avermectin B1a/B1b are dissolved in 0.3 ml of toluene, 18 mg of triphenylphosphine and 7.5 mg of pyrrole-2-carboxylic acid are added. The reaction mixture is stirred at room temperature under a blanket of nitrogen and 11.1 μl of diethylazodicarboxylate is added and the reaction mixture stirred for 20 minutes. The solvent is removed under a stream of nitrogen and the residue dissolved in methylene chloride and placed on a preparative layer chromatography plate coated with 1.5 mm of silica gel and eluted with a 7% methanol in methylene chloride. The band containing the product is extracted with ethyl acetate and evaporated to dryness affording 43 mg of a white foam which is identified using mass spectrometry and nuclear magnetic resonance as 22,23-dihydro-4a-(2-pyrrolecarbonyloxy) avermectin B1a/B1b.

EXAMPLE 5

22,23-Dihydro-4a-benzoyloxy Avermectin B1a/B1b 50 mg of 22,23-dihydro-4a-hydroxy avermectin B1a/B1b is dissolved in 0.25 ml of toluene and combined with 18 mg of triphenylphosphine and 8.2 mg of benzoic acid. The reaction mixture is stirred under a blanket of nitrogen and 11.1 μl of diethylazodicarboxylate is added and the reaction mixture is stirred at room temperature for 20 minutes. The solvent is evaporated under a stream of nitrogen and the residue dissolved in methylene chloride and placed equally on 2 preparative layer chromatography plates coated with 1 ml of silica gel and eluted with 7% methanol in methylene chloride. The band closest to the origin is removed with ethyl acetate, dissolved in a minimum amount of methylene chloride, and placed on single preparative layer chromatography plate coated with 1 mm of silica gel and eluted with 5% methanol in methylene chloride affording 40 mg of a clear glass which is identified using mass spectrometry and nuclear magnetic resonance as 22,23-dihydro-4a-benzoyloxy avermectin B1a/B1b.

EXAMPLE 6

22,23-Dihydro-4a[(3-pyridinylcarbonyl)oxy] avermectin B1a/B1b

Following the procedure of Example 5, using 50 mg of 22,23-dihydro-4a-hydroxy avermectin B1a/B1b, 0.3 ml of toluene, 18 mg of triphenylphosphine, 8.3 mg of pyridine-3-carboxylic acid and 11.1 μl of diethylazodicarboxylate, there is obtained after preparative layer chromatography 62 mg of a white foam identified by nuclear magnetic resonance as 22,23-dihydro-4a-[3-pyridinylcarbonyl)oxy] avermectin B1a/B1b.

EXAMPLE 7

4″,5-Di(phenoxyacetyl)-4a-hydroxy Avermectin B1a/B1b

Following the procedure of Example 1 using 11.1 mg of selenium dioxide 0.4 ml of methylene chloride, 45 μl of t-butylhydroperoxide and 230 mg of 4″,5-di(phenoxyacetyl) avermectin B1a/B1b there is obtained after 19 hours reaction at room temperature 235 mg of crude product. The crude product is dissolved in methylene chloride and placed equally on 2 preparative layer chromatography plates with 2 mm of silica gel coating and eluted with 4% methanol in methylene chloride. The band closest to the origin is removed from the plate with ethyl acetate and placed on a preparative layer chromatography plate with a 1.5 mm coating of silica gel and eluted with 4% methanol in chloroform affording 70 mg of a white glass which is identified using mass spectrometry and nuclear magnetic resonance as 4",5-di(phenoxyacetyl)-4a-hydroxy avermectin B1a/B1b.

EXAMPLE 8

4",5-Di(phenoxyacetyl)-4a-acetoxy Avermectin B1a/B1b 2 mg of 4",5-di(phenoxyacetyl)-4a-hydroxy avermectin B1a/B1b is combined with 4 drops of pyridine and 2 drops of acetic anhydride. The reaction mixture is stoppered and stirred at room temperature for 30 minutes. 2 Ml of water is added and the mixture extracted 3 times with 3 ml of ether. The ether layers are combined and washed 3 times with 1 ml of water, dried over magnesium sulfate and evaporated to dryness under a stream of nitrogen. The residue is dissolved in a minimum amount of methylene chloride and placed on 2 preparative layer chromatography plates coated with 250μ of silica gel and eluted with 20% ethyl acetate in chloroform. The band containing the product is removed with ethyl acetate affording 4",5-di(phenoxyacetyl)-4a-acetoxy avermectin B1a/B1b identified by nuclear magnetic resonance and mass spectrometry.

EXAMPLE 9

5,13-Di-O-acetyl-4a-hydroxy-22,23-dihydro avermectin B1a/B1b aglycone and 4a-13-di-O-acetyl-4a-hydroxy-22,23-dihydro Avermectin B1a/B1b aglycone Following the procedure of Example 1 using 5.5 mg of selenium dioxide, 0.1 ml of methylene chloride, 22 μl of 90% t-butyl hydroperoxide, 67 mg of 5,13-di-O-acetyl-22,23-dihydro avermectin B1a/B1b aglycone and 0.3 ml of methylene chloride there is obtained after 22 hours of stirring at room temperature 68 mg of a yellow foam which is dissolved in chloroform and placed on a single preparative layer chromatography plate with a 1 mm coating of silica gel and eluted with 5% methanol in methylene chloride. The band closest to the origin is removed with ethyl acetate and evaporated to dryness affording 15 mg of an off-white glass which is identified by mass spectrometry and nuclear magnetic resonance as 5,13-di-O-acetyl-4a-hydroxy-22,23-dihydro avermectin B1a/B1b aglycone. The band next closest to the origin is similarly removed affording 9.5 mg of material which is identified using mass spectrometry or nuclear magnetic resonance as 4a-13-di-O-acetyl-4a-hydroxy-22,23-dihydro avermectin B1a/B1b aglycone.

EXAMPLE 10

4a,5,13-Tri-O-acetyl-22,23-dihydro-4a-hydroxy avermectin B1a/B1b aglycone 2 mg of 5,13-di-O-acetyl-22,23-dihydro-4a-hydroxy avermectin B1a/B1b aglycone is combined with 4 drops of pyridine, 2 drops of acetic anhydride, stoppered, and allowed to stand at room temperature for 30 minutes. An equal volume of water is added and the mixture is extracted 3 times with ether and the combined ether extracts are washed 3 times with 1 ml portions of water. The ether layer is dried over magnesium sulfate and evaporated in a stream of nitrogen affording 4a,5,13-tri-O-acetyl-22,23-dihydro-4a-hydroxy avermectin B1a/B1b aglycone which is identified using nuclear magnetic resonance.

EXAMPLE 11

4",5-Di-O-phenoxyacetyl-22,23-dihydro-4a-hydroxy avermectin B1a/B1b

Following the procedure of Example 1 using 75 mg of selenium dioxide and 4.5 ml of methylene chloride, 0.3 ml of t-butyl hydroperoxide and 1.14 gms of 4",5-di-O-phenoxyacetyl-22,23-dihydro avermectin B1a/B1b in 1.5 ml of methylene chloride there is obtained after the reaction period of 48 hours 1.13 gms of crude product. Crude material is placed on a column of 65 gms of silica gel and eluted with 15% ethyl acetate in methylene chloride. The first 200 ml is discarded and 20 ml cuts are taken thereafter. Fractions 47 to 60 afford 222 mg of a light yellow foam which is identified by nuclear magnetic resonance and mass spectroscopy as 4",5-di-O-phenoxyacetyl-22,23-dihydro-4a-hydroxy avermectin B1a/B1b.

EXAMPLE 12

13-Deoxy-22,23-dihydro-4a-hydroxy Avermectin B1a/B1b aglycone

Following the procedure of Example 1 using 28 mg of selenium dioxide, 2.5 ml of methylene chloride, 0.11 ml of t-butyl hydroperoxide and 285 mg of 13-deoxy-22,23-dihydro avermectin B1a/B1b aglycone there is obtained after 19 hours of reaction 380 mg of crude product. The crude product is dissolved in methylene chloride and placed equally on 3 preparative layer chromatography plates with 2 ml of silica gel coating and eluted with 7% methanol in methylene chloride. The second slowest fraction is removed from the chromatography plate with ethyl acetate affording 90 mg of 13-deoxy-22,23-dihydro-4a-hydroxy avermectin B1a/B1b aglycone which is identified by mass spectrometry, nuclear magnetic resonance and ultraviolet spectroscopy.

EXAMPLE 13

13-Deoxy-22,23-dihydro-4a-(2-pyrrolecarbonyloxy) Avermectin B1a/B1b aglycone

Following the procedure of Example 4, using 40 mg of 13-deoxy-22,23-dihydro-4a-hydroxy avermectin B1a/B1b aglycone, 24 mg of triphenylphosphine, 10 mg of pyrrole-2-carboxylic acid, 15 μl of diethylazodicarboxylate and 0.4 ml of toluene there is obtained after a reaction period of 20 minutes and preparative layer chromatography on 2 mm of silica gel eluting with 6% methanol in methylene chloride, 24 mg of 13-deoxy-22,23-dihydro-4a-(2-pyrrolecarbonyloxy) avermectin B1a/B1b aglycone which is identified using mass spectrometry and nuclear magnetic resonance.

EXAMPLE 14

4a-hydroxymilbemycin α₁

53 Mg of milbemycin $\alpha_1$ is dissolved in 0.2 ml of methylene chloride and added to a mixture of 5.5 mg of selenium dioxide, 3 ml of methylene chloride and 22 μl of t-butyl hydroperoxide and stirred at 18° C. for 24 hours. Then 4 ml of water and 3 ml of ether are added and the mixture is shaken in a stoppered 15 ml centrifuge tube. The layers are separated and the aqueous layer is extracted twice again with 2 ml of ether. The ether extracts are combined and washed three times with 1 ml of water, dried over magnesium sulfate and concentrated under a stream of nitrogen. The residue is separated on three 20 cm preparative layer chromatography plates with a 500 μ silica gel layer and eluted with methylene chloride containing 7% methanol. One slow moving band is separated, identified as 4a-hydroxymilbemycin $α_1$ by nuclear magnetic resonance and mass spectral analysis.

EXAMPLE 15

4a-Hydroxymilbemycin $α_3$

When 54 mg of milbemycin $α_3$ are subjected to the procedure of Example 14 one obtains 4a-hydroxymilbemycin $α_3$.

Following the above procedure employing 23-ketoavermectin B2a/B2b in place of milbemycin $α_3$, there is obtained 4a-hydroxy-23-keto avermectin B2a/B2b.

EXAMPLE 16A

4a-Hydroxy-4a-O-[3-[(2,2,2-trichloroethoxy)carbonyl]-propanoyl] milbemycin $α_1$ A mixture of 41 mg of 4a-hydroxymilbemycin $α_1$, 27 mg of triphenylphosphine, 25 mg of 3-[(2,2,2-trichloroethoxy)carbonyl] propanoic acid is stirred with 0.5 ml of toluene at 18° C. under a blanket of nitrogen. 15 Microliters of diethylazodicarboxylate is added. After 20 minutes, 1 ml of ether is added and the mixture is centrifuged and the solution is applied to one 20×20 cm silica gel preparative layer chromatography plate with a 2 mm coating. After development with methylene chloride containing 7% methanol the fluorescent band containing the milbemycin derivative is extracted with ethyl acetate. The extract is further purified by preparative thin layer chromatography on a 1 mm silica gel coated plate developed with a one-to-one mixture of methylene chloride and ethyl acetate giving essentially pure 4a-hydroxy-4a-O-[3-[(2,2,2-trichloroethoxy)carbonyl]propanoyl]milbemycin $α_1$ identified by nuclear magnetic resonance and mass spectrometry.

EXAMPLE 16B

4a-Hydroxy-4a-O-succinoyl milbemycin $α_1$

A solution of 35 mg of the product of Example 16A is dissolved in 1.5 ml of glacial acetic acid and stirred vigorously with 200 mg of zinc dust for one hour at 18° C. The reaction mixture is filtered and the filtrate is concentrated under high vacuum. The residue is taken up in ethyl acetate washed with dilute hydrochloric acid and water, dried and concentrated in vacuo. The residue is purified by preparative layer chromatography on silica gel eluting with a mixture of methylene chloride, tetrahydrofuran and acetic acid to give 4a-hydroxy-4a-O-succinoyl milbemycin $α_1$ identified by nuclear magnetic resonance and mass spectometry.

EXAMPLE 17

4a-Hydroxy-4a-O-glutaryl avermectin A2a/A2b Sodium Salt

92 Mg of 4a hydroxy avermectin A2a/A2b is dissolved in 2.0 ml of pyridine. 22 Mg of glutaric anhydride and 4 mg 4-dimethylaminopyridine is added and the mixture is heated for 3 hours at 100° C. The solvent is evaporated under high vacuum and the residue is dissolved in ethyl acetate. The solution is washed repeatedly with dilute hydrochloric acid in water, dried and concentrated in vacuo. The residue is further purified by preparative thin layer chromatography on silica gel eluting with a mixture of methylene chloride, tetrahydrofuran and acetic acid to give 4a-hydroxy-4a-O-glutaryl avermectin A2a/A2b which is characterized in the usual way by nuclear magnetic resonance and mass spectrometry. 52 Mg of this acid is dissolved in 3 ml of methanol and treated with 0.5 ml of a 0.1 N aqueous solution of sodium hydroxide and the solution again concentrated in vacuo and under high vacuum to give 4a-hydroxy-4a-O-glutaryl avermectin A2a/A2b sodium salt.

EXAMPLE 18

4a Hydroxy 4a-O-adipoyl avermectin B1a/B1b Ammonium Salt

A solution of 89 ml of 4a-hydroxy avermectin B1A/B1b, 25 mg of 4-dimethylaminopyridine and 15 mg of adipic acid in 1.5 ml of methylene chloride is stirred at room temperature. To this a solution of 46 mg of dicyclohexylcarbodiimide is added and the reaction mixture is stirred for 90 minutes at 18° C. Then about 80 ml of ether is added and the mixture is transferred into a separatory funnel. It is washed repeatedly with dilute aqueous hydrochloric acid and with water, dried and concentrated in vacuo and under high vacuum. Final purification by preparative layer silica gel chromatography affords 4a-hydroxy-4a-O-adipoyl avermectin B1a/B1b characterized by nuclear magnetic resonance and mass spectrometry. The free acid is taken up in about 5 ml of methanol, treated with a few drops of aqueous ammonium hydroxide solution and the solution concentrated in vacuo and under high vacuum to give 4a hydroxy 4a-O-adipoyl avermectin B1a/B1b ammonium salt.

EXAMPLE 19

13-deoxy-4a-hydroxy-5-O-t-butyldimethylsilyl-22,23-dihydro avermectin B1a/B1b aglycone A mixture consisting of 55 mg of selenium dioxide 4.5 ml of methylene chloride and 0.22 ml of 90% t-butylhydroperoxide and 684 mg of 13-deoxy-5-O-t-butyldimethylsilyl-22,23-dihydro avermectin B1a/B1b aglycone is stirred at 18° C. for 24 hours, then water is added and the reaction mixture is extracted with ether. The ether extract is washed with water, dried and concentrated in vacuo to a light foam. Preparative layer chromatography on 2 mm thick silica oel plates, eluting with methylene chloride containing 6% methanol, allows for the isolation of pure 13-deoxy-4a-hydroxy-5-O-t-butyldimethylsilyl 22,23-dihydro avermectin B1a/B1b aglycone identified from its nuclear magnetic resonance and mass spectrometry data.

EXAMPLE 20

13-deoxy-4a-hydroxy-4a-O-succinoyl-5-O-t-butyldimethylsilyl-22,23-dihydro avermectin B1a/B1b Aglycone A solution of 70 mg of 4a-hydroxy-5-O-t-butyldimethylsilyl-22,23-dihydro avermectin B1a/B1b aglycone. 30 Mg of succinic anhydride 3 mg of 4-dimethylaminopyridine in 1 ml of pyridine is heated to 100° C. for 3 hours and concentrated under high vacuum. The residue is dissolved in ether and washed with dilute hydrochloric acid and water. The ether extract is dried, concentrated in vacuo and purified by preparative layer chromatography to give 13-deoxy-4a-hydroxy-4a-O-succinoyl-5-O-t-butyldimethylsilyl-22,23-dihydro avermectin B1a/B1b aglycone which is characterized by its nuclear magnetic resonance and mass spectral data.

EXAMPLE 21

13-deoxy-4a-hydroxy-4a-O-succinoyl-22,23-dihydro avermectin B1a/B1b aglycone

The compound of Example 20 is dissolved in 3 ml of methanol containing 1% of p-toluenesulfonic acid and kept at 18° C. for 30 minutes. It is then concentrated under a stream of nitrogen at 18° C. and the residue applied to preparative layer silica gel chromatography plates and developed with a mixture of methylene chloride, tetrahydrofuran and acetic acid. The band containing the product is removed by extraction with ethyl acetate to afford 13-deoxy-4a-hydroxy-4a-O-succinoyl-22,23-dihydro avermectin B1a/B1b aglycone which structure is confirmed by nuclear magnetic resonance and mass spectrometry.

Preparation 1

4",5-Di-O-phenoxyacetyl Avermectin B1a/B1b

1 Gm of avermectin B1a/B1b in 10 ml of methylene chloride is treated with 0.25 ml of pyridine and cooled under a blanket of nitrogen in an ice bath. 10 ml of methylene chloride containing 0.39 ml of phenoxyacetyl chloride is added dropwise over a 45 minute period and the reaction mixture is allowed to rise to room temperature and stirred for 2 hours. After 24 hours 100 ml of ice water is added and an equal volume of ether and the mixture shaken and the layers separated. Aqueous layer is extracted 3 more times with ether and the ether layers are combined and washed 4 times with water and once with saturated sodium chloride solution. The ether layer is dried over magnesium sulfate and evaporated to dryness in vacuo affording 1.44 gms of a white foam. The crude material is placed on a column of 50 gms of silica gel and eluted with 12% ethyl acetate in methylene chloride taking 10 ml cuts. Fractions 9-30 are collected affording 470 mg of a white foam identified by mass spectrometry and nuclear magnetic resonance as 4",5-di-O-phenoxyacetyl avermectin B1a/B1b.

Preparation 2

4",5-Di-O-phenoxyacetyl-22,23-dihydro Avermectin B1a/B1b

Following the procedure of Preparation 1 using 3 gms of 22,23-dihydro avermectin B1a/B1b, 20 ml of methylene chloride, 0.76 ml of pyridine and 1.18 ml of phenoxyacetylchloride and 20 ml of methylene chloride, there is obtained after column chromatography on 200 gms of silica gel eluting with 8% ethyl acetate in methylene chloride, 3.74 gms of 4",5-di-O-phenoxyacetyl-22,23-dihydro avermectin B1a/B1b identified by mass spectrometry and nuclear magnetic resonance.

Preparation 3

5,13-Di-O-acetyl-22,23-dihydro Avermectin B1a/B1b aglycone

To 500 mg of 22,23-dihydro avermectin B1a/B1b aglycone and 6 ml of pyridine cooled in an ice bath is added dropwise 3 ml of acetic anhydride. The reaction mixture is allowed to stir at room temperature for 4 hours and at −5° C. overnight. The reaction mixture is poured onto 90 ml of cold water and extracted 4 times with ether. The combined ether extracts are washed 5 times with 15 ml portions of water and once with saturated sodium chloride solution. Ether layers are dried over magnesium sulfate and evaporated to dryness in vacuo affording 670 mg of crude product. Crude product is purified on a column of 22 gms of silica gel eluting with 10% ethyl acetate in methylene chloride. The first 120 ml of eluate is concentrated affording 550 mg of 5,13-di-O-acetyl-22,23-dihydro avermectin B1a/B1b aglycone identified by nuclear magnetic resonance and mass spectroscopy.

Preparation 4

23-Keto-avermectin B2a/B2b

A.

4",5-Di-O-(tert-butyl-dimethylsilyloxyacetyl)avermectin B2a/B2b

In a flame dried reaction vessel containing dry nitrogen are combined 2.0 gm of avermectin B2a/B1b, 25 ml of diethyl ether and 2.5 ml of dry pyridine. The solution is cooled to 0° C. in an ice bath and 8 ml of a diethyl ether solution containing 940 mg of tert-butyl dimethylsilyloxyacetyl chloride is added. The addition produces a white precipitate. The reaction mixture is stirred for 30 minutes in an ice bath after which thin layer chromatographic analysis indicates that the reaction is not yet complete. An additional 8 ml of an ether solution containing 100 mg of tert-butyl dimethylsilyloxyacetyl chloride per ml of solution is added and the reaction mixture stirred for an additional 80 minutes. Thin layer chromatographic analysis indicates the absence of starting material in the reaction mixture. 200 Ml of cold water is added to the reaction mixture which is then extracted 5 times with 100 ml portions of diethyl ether. The combined ether extracts are washed 7 times with 20 ml portions of water and once with a 1:1 mixture of water and aqueous saturated sodium chloride. The ether layer is dried over magnesium sulfate, evaporated to dryness in vacuo and dried under high vacuum affording 3.2 g of a clear white foam which is purified on a column of 175 g of silica gel eluting with 15% ethyl acetate in methylene chloride. The first 500 ml of eluant is discarded and 20 ml fractions are collected thereafter. Fractions 39–63 are collected affording 1.34 g of a white foam which is characterized by mass spectrometry, and 300 MHz nuclear magnetic resonance spectrometry to be 4"-5-di-O-(tert-butyldimethylsilyloxyacetyl)-avermectin B2a/B2b.

B.

4",5-Di-O-(tert-butyl-dimethylsilyloxyacetyl)-23-keto-avermectin B2a/B2b 12.4 Mg (0.01 mmoles) of 4",5-di-O-(tertbutyldimethylsilyloxyacetyl)avermectin B2a/B2b is dissolved in 0.5 ml of dry dimethylformamide and 37.6 mg (0.1 mmoles) of pyridinum dichromate is added in one portion with stirring at room temperature. The reaction mixture is stirred at room temperature for 3 ½ hours. An aliquot is removed and analyzed on a thin layer chromatograpy silica gel plate and shows no starting material. The reaction is diluted with 5 ml of ice water and extracted three times with ether. The ether extracts are washed twice with water and once with saturated sodium chloride. After drying with magnesium sulfate and evaporation to dryness in vacuo, there is recovered 10.5 mg of a white foam. The foam is purified on a preparative layer chromatograpy plate with 250μ of silica gel and eluted with 5% tetrahydrofuran and 0.15% ethanol in methylene chloride. The product band is removed from the plate using 25% ethyl acetate in methylene chloride, filtered and evaporated to dryness affording 7.0 mg of a white glass which is identified with mass spectrometry and 300 MHz nuclear magnetic resonance spectra as 4",5-di-O-(tert-butyldimethyl-silyloxyacetyl)-23-keto-avermectin B2a/B2b.

C. 4",5-Di-(O-hydroxyacetyl)-23-keto avermectin B2a/B2b 4.6 Mg (0.0037 mmoles) of 4",5-di-O-(tertbutyldimethylsilyloxyacetyl)-23-keto-avermectin B2a/B2b is dissolved in 1.38 ml of 1% p-toluenesulfonic acid in methanol and stirred at room temperature for 55 minutes. The reaction mixture is diluted with 5 ml of dilute sodium bicarbonate (prepared from 0.5 ml of saturated sodium bicarbonate and 4.5 ml of water) and extracted three times with ether. The ether is washed three times with water, once with saturated sodium chloride, dried and evaporated to dryness in vacuo affording 4.8 mg of a yellow foam which is used without further purification in the next step.

D. 23-Keto-avermectin B2a/B2b 4.8 Mg (0.0048 mmoles) of the product from Preparation 4 part C is dissolved in 0.5 ml of dry methanol and 39 μl (0.0048 mmoles) of a sodium methoxide in methanol solution (prepared from 28 mg of sodium and 10 ml of dry methanol). The reaction is stirred at room temperature for 90 minutes. The reaction mixture is diluted with 5 ml of water containing 1 drop of acetic acid and extracted three times with ether. The ether extracts are washed three times with water, once with dilute sodium bicarbonate, once with saturated sodium chloride solution, dried over magnesium sulfate and evaporated in a stream of nitrogen. The residue is dried under high vacuum affording 2.9 mg of a glassy residue. The residue is purified on a preparative layer chromatography plate coated with 250μ of silica gel, eluting with 5% methanol in chloroform. The bands containing product are located under ultraviolet light and removed from the silica gel with ethyl acetate. Three bands are isolated on the plate and the middle band is 23-keto-avermectin B2a/B2b as determined by the 300 MHz nuclear magnetic resonance spectrum. 1.5 Mg are isolated.

Preparation 5

Avermectin B2a/B2b 4",5-Di-O-Acetate

200 Mg of avermectin B2a/B2b is dissolved in 3 ml of dry pyridine and cooled in an ice bath. 1 Ml of acetic anhydride is added and the reaction mixture is allowed to stand at 0° C. overnight. The reaction mixture is combined with benzene and lyophilized and the solid material purified by preparative layer chromatography on silica gel plates eluting with 5% tetrahydrofuran in chloroform affording 208 mg of a white solid identified by mass spectrometry as avermectin B2a/B2b 4",5-di-O-acetate.

Preparation 6

23-Keto-avermectin-B2a/B2b-4",5-di-O-Acetate

A solution of 100 g of avermectin B2a/B2b 4",5-di-O-acetate in 0.5 ml of methylene chloride is added at −70° C. to a solution of oxidizing agents prepared at −70° C. from 20 μl of oxalyl chloride and 32 μl of dimethylformamide in 0.7 ml of methylene chloride. The reaction mixture is kept at −70° to −50° C. for 30 minutes, then 0.15 ml of triethylamine is added, and after 5 minutes at −50° to −70° C. the reaction mixture is allowed to warm up to room temperature. The mixture is poured onto ice water and extracted with methylene chloride and further purification by preparative layer chromatography on silica gel gives 23-keto-avermectin-B2a/B2b-4",5-di-O-acetate, which is identified by its NMR and mass spectra.

What is claimed is:

1. A compound having the formula:

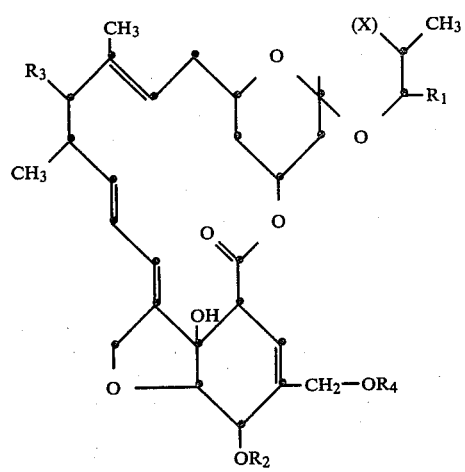

wherein
X is $-CH_2-CH_2-$ $-CH_2-\overset{OH}{\underset{|}{CH}}-$, $-CH=CH-$, or -continued

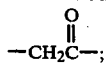

$R_1$ is methyl, ethyl, isopropyl or sec-butyl;

$R_2$ is hydrogen, methyl, acetyl, phenoxyacetyl or tert-butyl dimethylsilyl;

$R_3$ is hydrogen, hydroxy, acetoxy, α-L-oleandrosyloxy, 4'-acetyl-α-L-oleandrosyloxy, 4'-(α-L-oleandrosyl)-α-L-oleandrosyloxy, 4''-acetyl-4'-(α-L-oleandrosyl)-α-L-oleandrosyloxy, or 4''-(phenoxy-acetyl)-4'-(α-L-oleandrosyl)-α-L-oleandrosyloxy; and $R_4$ is hydrogen, acetyl, benzoyl, —CO(CH$_2$)$_n$COOH, or —CO(CH$_2$)$_n$COOM, wherein n is 2, 3 or 4 and M is an alkali metal or an ammonium or diloweralkyl ammonium cation;

provided that $R_4$ is

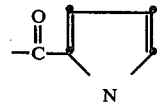

only when $R_1$ is isopropyl or sec-butyl.

2. The compound of claim 1 wherein X is —CH=CH—.

3. The compound of claim 2 which is 4a-hydroxy-avermectin B1a/B1b.

4. The compound of claim 1 wherein X is —CH$_2$—CH$_2$—.

5. The compound of claim 4 which is 4a-hydroxy-22,23-dihydro avermectin B1a/B1b.

6. The compound of claim 4 which is 4a[(2-pyrrollyl-carbonyl)oxy]-22,23-dihydro avermectin B1a/B1b.

7. The compound of claim 4 which is 4a-hydroxy-13-deoxy-22,23-dihydro avermectin B1a/B1b aglycone.

8. The compound of claim 4 which is 4a-hydroxy-4a-O-succinoyl-22,23-dihydro avermectin B1a/B1b or the sodium salt thereof.

9. The compound of claim 1 wherein $R_3$ is hydrogen.

10. A method for the treatment of parasitic infections which comprises administering to an animal infected with parasites, an effective amount of a compound of claim 1.

11. A composition useful for treating animals infected with parasites which comprises an inert carrier and an effect amount of a compound of claim 1.

* * * * *